United States Patent
Devic

(10) Patent No.: US 8,062,606 B2
(45) Date of Patent: Nov. 22, 2011

(54) COATED REACTORS, PRODUCTION METHOD THEREOF AND USE OF SAME

(75) Inventor: Michel Devic, Sainte Foy les Lyon (FR)

(73) Assignee: Arkema France, Colombes (FR)

( * ) Notice: Subject to any disclaimer, the term of this patent is extended or adjusted under 35 U.S.C. 154(b) by 261 days.

(21) Appl. No.: 12/513,412

(22) PCT Filed: Nov. 6, 2007

(86) PCT No.: PCT/FR2007/052304
§ 371 (c)(1),
(2), (4) Date: May 4, 2009

(87) PCT Pub. No.: WO2008/059154
PCT Pub. Date: May 22, 2008

(65) Prior Publication Data
US 2010/0068108 A1 Mar. 18, 2010

(30) Foreign Application Priority Data
Nov. 14, 2006 (FR) ...................................... 06 54878

(51) Int. Cl.
*B01J 19/02* (2006.01)
(52) U.S. Cl. ........................................ 422/240; 422/241
(58) Field of Classification Search .................. 422/240, 422/241
See application file for complete search history.

(56) References Cited

U.S. PATENT DOCUMENTS

| | | | |
|---|---|---|---|
| 2,970,042 A * | 1/1961 | Lagerwey | 422/241 |
| 3,135,420 A | 6/1964 | Farell et al. | |
| 3,779,854 A | 12/1973 | Dukert et al. | |
| 3,824,115 A | 7/1974 | Segawa et al. | |
| 4,166,536 A | 9/1979 | Roberts et al. | |
| 5,522,522 A * | 6/1996 | Fukumoto | 220/62.22 |
| 5,902,912 A | 5/1999 | Tung et al. | |
| 6,939,521 B1 * | 9/2005 | Chiu et al. | 422/203 |
| 2004/0101448 A1 | 5/2004 | Yuichi et al. | |
| 2006/0122333 A1* | 6/2006 | Nishio | 525/199 |
| 2007/0275225 A1* | 11/2007 | Devic et al. | 428/299.1 |
| 2010/0068108 A1* | 3/2010 | Devic | 422/241 |

FOREIGN PATENT DOCUMENTS

| | | |
|---|---|---|
| FR | 1057247 A * | 3/1954 |
| FR | 2277004 | 1/1976 |
| FR | 2374433 | 7/1978 |
| FR | 2864465 A1 * | 7/2005 |
| JP | 7-233102 | 9/1995 |

* cited by examiner

Primary Examiner — Jennifer A Leung
(74) Attorney, Agent, or Firm — Steve D. Boyd

(57) ABSTRACT

The invention relates to coated reactors resistant to acid corrosion, the production method thereof and the use of same in processes in superacid media. More specifically, the invention relates to a reactor comprising an inner metal wall having a fluoropolymer coating anchored thereto using a perforated sheet positioned between the inner metal wall and the fluoropolymer coating. The surface of the sheet that is in contact with the metal wall of the reactor has a sufficient roughness in order to form a free space (for gases) between same and the metal wall of the reactor. In addition, the reactor is provided with a device for maintaining the pressure in the free space below that in the reactor.

9 Claims, 3 Drawing Sheets

COATED REACTORS, PRODUCTION METHOD THEREOF AND USE OF SAME

FIELD OF THE INVENTION

The present invention relates to coated reactors that are resistant to acid corrosion, to their method of manufacture and their uses in processes performed in a superacid medium.

PRIOR ART AND TECHNICAL PROBLEM

Reactions in a superacid medium, in particular fluorination reactions in the liquid phase, require, in order to be effective, the use of a reaction medium rich in HF and $SbCl_5$ (or $SbCl_xF_y$) and high temperatures (80 to 120° C.). Anhydrous HF in the liquid phase forms a very corrosive superacid medium with $SbCl_5$. The usual corrosion-resistant metals and alloys such as stainless steels, Inconels, nickel, Hastelloys, etc. do not have sufficient resistance to produce an industrial reactor.

One solution (JP 07-233102) consists in applying a fluoropolymer coating to the inside of a stainless steel reactor. Another solution (U.S. Pat. No. 4,166,536, U.S. Pat. No. 3,824,115) consists in using a fluoropolymer containing particles of inorganic substances such as silica, graphite or carbon.

However, the application of this type of coating to the inside of the reactor raises numerous technical problems as highlighted by patent WO 99/00344:

The polymer deposits obtained by spraying and melting of polymer powder are porous, the metal is attacked by HF and the coating becomes detached.

The deposits obtained by melting and rotomolding are thicker and more impervious, but this technique is limited to small-sized reactors (3785 liters) and, in addition, these coatings, even thick coatings are still slightly permeable and acids eventually penetrate between the polymer layer and the metal wall of their reactor and overpressures are created and cause considerable swelling and deformation of the fluoropolymer coating.

Patent WO 99/00344 proposes to discharge these overpressures by drilling small holes in the wall of the reactor (0.31 cm to 1.27 cm in diameter).

The use of a fluoropolymer coating in an industrial reactor is moreover only possible at the present time at low temperature (20 to 40° C.) since the expansion coefficient of the fluoropolymers is much higher than that of steel. At the temperatures necessary for the liquid-phase fluorination of chloroalkanes (80 to 120° C.), the expansion of the coating is very high and causes structural damage (folds, tension, deformation, tears, stripping) aggravated by the low mechanical strength of the polymer when hot.

Furthermore, the problems of differential expansion between the polymer and the metal in the reactors which lead to detachments and stripping of the coating are known. Solutions that use multilayer coatings of fluoropolymers, and resin (U.S. Pat. No. 3,779,854) and glass fibers exist but are totally unsuitable for carrying out reactions in a superacid medium such as HF.

Therefore, to date no satisfactory solution has been found for producing reactors that are resistant both chemically and mechanically to superacid corrosive media.

The objective of the invention is to provide coated reactors that are resistant both mechanically and chemically to acid corrosive media.

DETAILED DESCRIPTION OF THE INVENTION

Figure 1:
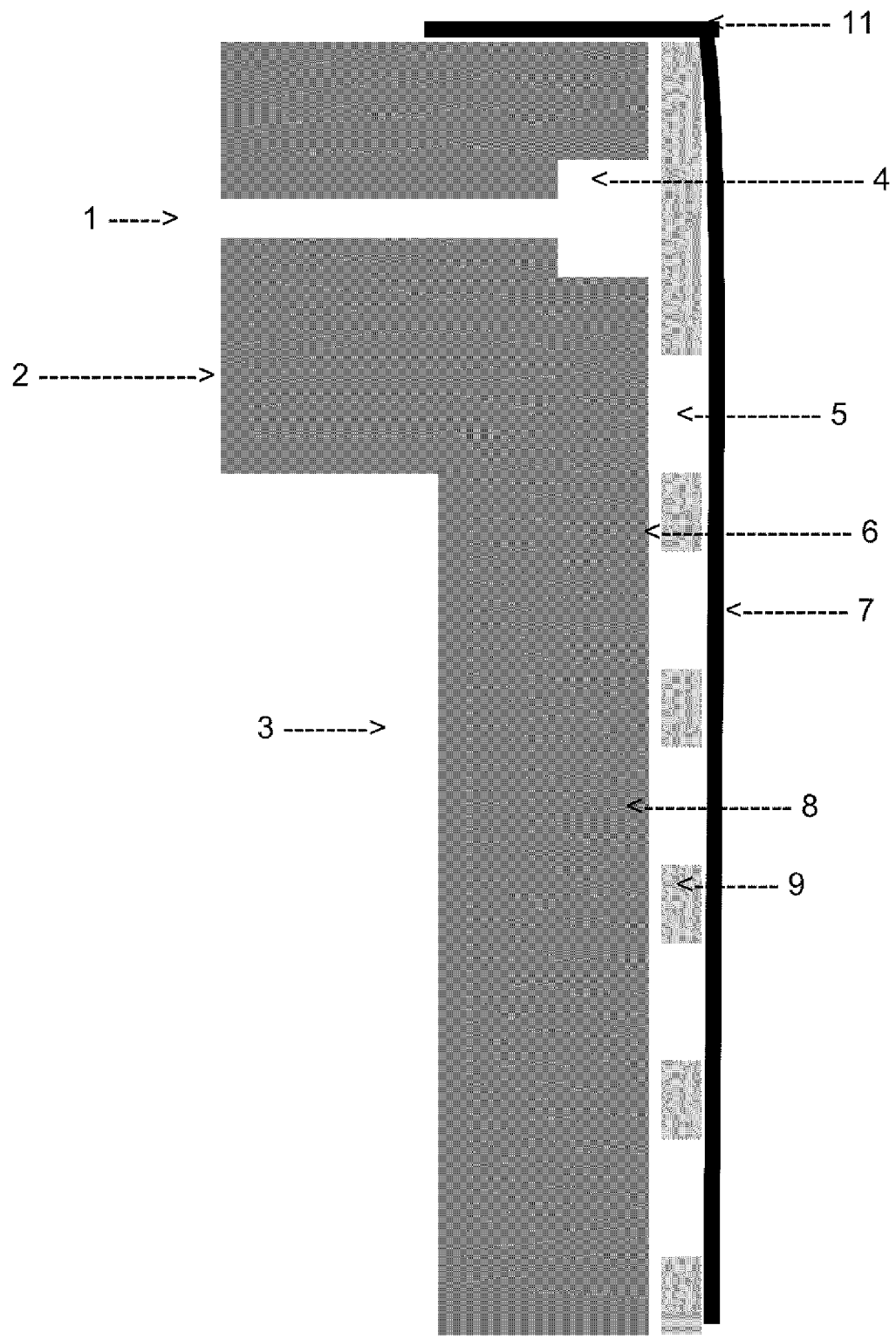
FIG. 1 is a vertical cross section of the coated reactor.

The invention therefore relates to a reactor comprising an inner metal wall anchored to which is a fluoropolymer coating, the anchoring being provided by a perforated metal sheet located between the inner metal wall and the fluoropolymer coating, and the face of said sheet in contact with the metal wall of the reactor has a sufficient roughness to act as a free space (for gases) between it and the metal wall of the reactor; the reactor is equipped with a device that makes it possible to maintain the pressure in the free space below that of the reactor.

Orifices may be made in the metal wall of the reactor to control said pressure.

The edges of the holes of the sheet in contact with the fluoropolymer coating are preferably slightly rounded in order to prevent any shearing which could damage the coating.

The perforated sheet may be provided with vertical ribs, which are preferably arranged uniformly.

The ribs having a section that is preferably semi-circular or trapezoidal, and advantageously of 0.1 to 1 $cm^2$ are made, especially by drawing or bending during the manufacture of the perforated sheet, in zones of the sheet that do not have any holes. The spacing between the ribs is preferably between 10 and 50 cm.

The thickness of the fluoropolymer coating may be from 1 to 10 mm and preferably 1.5 to 5 mm.

The fluoropolymers (FPs) used in the invention are thermoplastic polymers that are resistant to acid media, in particular chosen from the group consisting of polychloro-trifluoroethylene (PCTFE), copolymers of tetrafluoroethylene and perfluoropropene (FEP), copolymers of tetrafluoroethylene and perfluoro(propyl vinyl ether) (PFA), copolymers of tetrafluoroethylene and ethylene (ETFE), polymers of trifluorochloroethylene and ethylene (E-CTFE) and mixtures thereof.

Preferably, the fluoropolymer used is the copolymer of tetrafluoroethylene and hexafluoropropylene (FEP) for its properties of not allowing antimony (Sb) to diffuse into the polymer. The FEP used has 10 to 15% and preferably 12% by weight of hexafluoropropylene.

The thickness of the perforated sheet may be from 1 to 10 mm and preferably 3 to 6 mm. Advantageously, this thickness is close to that of the fluoropolymer coating.

The diameter of the holes in the perforated sheet, when they are circular, may be from 10 to 50 mm and preferably 15 to 30 mm.

The holes may also be of oblong, square or rectangular shape.

The holes may be made by drilling and chamfering the edge, by punching or by stamping.

The surface occupied by the holes may represent between 10 and 50% and preferably between 30 and 40% of the total surface of the perforated sheet.

The perforated metal sheet is preferably made in stainless steel.

The method of manufacturing the coated reactor comprises a step during which the inner metal wall of the reactor is brought into contact with the rough face of a perforated sheet, and the other free face of the sheet being brought into contact with the fluoropolymer coating, followed by an anchoring step during which the fluoropolymer coating sinks through the holes of the sheet and thus comes to rest on the inner wall of the reactor under the action of heat and pressure.

The inner wall of the reactor may be coated over its entirety or over only the portion in contact with the corrosive medium (liquid phase). Advantageously, the inner wall is only coated over the chamber of the reactor.

The coating is attached in an impervious manner to the top of the chamber using customary devices, for example: the upper edge of the coating may be formed as a flared flange, the angle of which is preferably between 45° and 90°, between one or two polytetrafluoroethylene (PTFE) seals compressed by the positioning of the lid of the reactor.

The inner wall of the cover may also comprise a coating made of FEP or any other fluoropolymer that is resistant to the superacid reaction medium. The coating may be simply attached by conventional means or by anchoring as described for the reactor chamber.

One or more circular grooves, preferably having a section between 0.2 and 2 cm$^2$, may be machined in the inner wall of the reactor, preferably perpendicular to the ribs of the perforated sheet, in order to collect the gases recovered by the ribs. Orifices made through the metal wall of the reactor make it possible to connect these grooves via pipes to the device for controlling the pressure that exists between the coating and the inner metal wall of the reactor. Advantageously, an orifice is made in the bottom of the reactor in order to recover the liquid condensates.

Advantageously, the groove is machined level with the clamp of the chamber seal.

The coated reactors as described above are capable of withstanding the conditions of reactions in a superacid medium, in particular the liquid-phase fluorination reactions, such as temperatures ranging from 0 to 150° C. and preferably 60 to 120° C. and a pressure of 1 to 15 bar absolute.

To improve the thermal conductivity of such a reactor, the fluoropolymer coating may be filled with carbon nanotubes.

The term "nanotubes" is understood to mean tubes or hollow fibers having a diameter of around 5 to 20 nanometers (nm) and having a length of around 100 to 1000 times the diameter.

Carbon has three well-known allotropic forms: amorphous carbon, graphite and diamond. Graphite is found in very light and strong carbon fibers. Diamond is commonly used for its exceptional mechanical properties, and for its high thermal conductivity. Carbon nanotubes, a new allotropic form of carbon, are considered to be a unique species of carbon-containing systems located mid-way between conventional carbon fibers and the new forms of carbon such as fullerenes. Their length to diameter ratio is so large that they can be considered, with respect to certain properties, as one-dimensional structures. There are two types of carbon nanotubes: single-walled and multi-walled nanotubes.

Diameter: a few nanometers for single-walled nanotubes and around 10 to a few tens of nanometers for multi-walled nanotubes.

Length: several microns.

A single-walled carbon nanotube, in the case where it is perfect, may be defined as a sheet of graphene rolled up and sealed to itself thus forming a cylinder composed solely of carbon atoms. The ends are formed from two carbon-based hemispheres.

A multi-walled nanotube is a concentric stack of single-walled nanotubes.

Another subject of the present invention is a reactor comprising the coating made from a fluoropolymer filled with carbon nanotubes.

Embodiment

Figure 2:
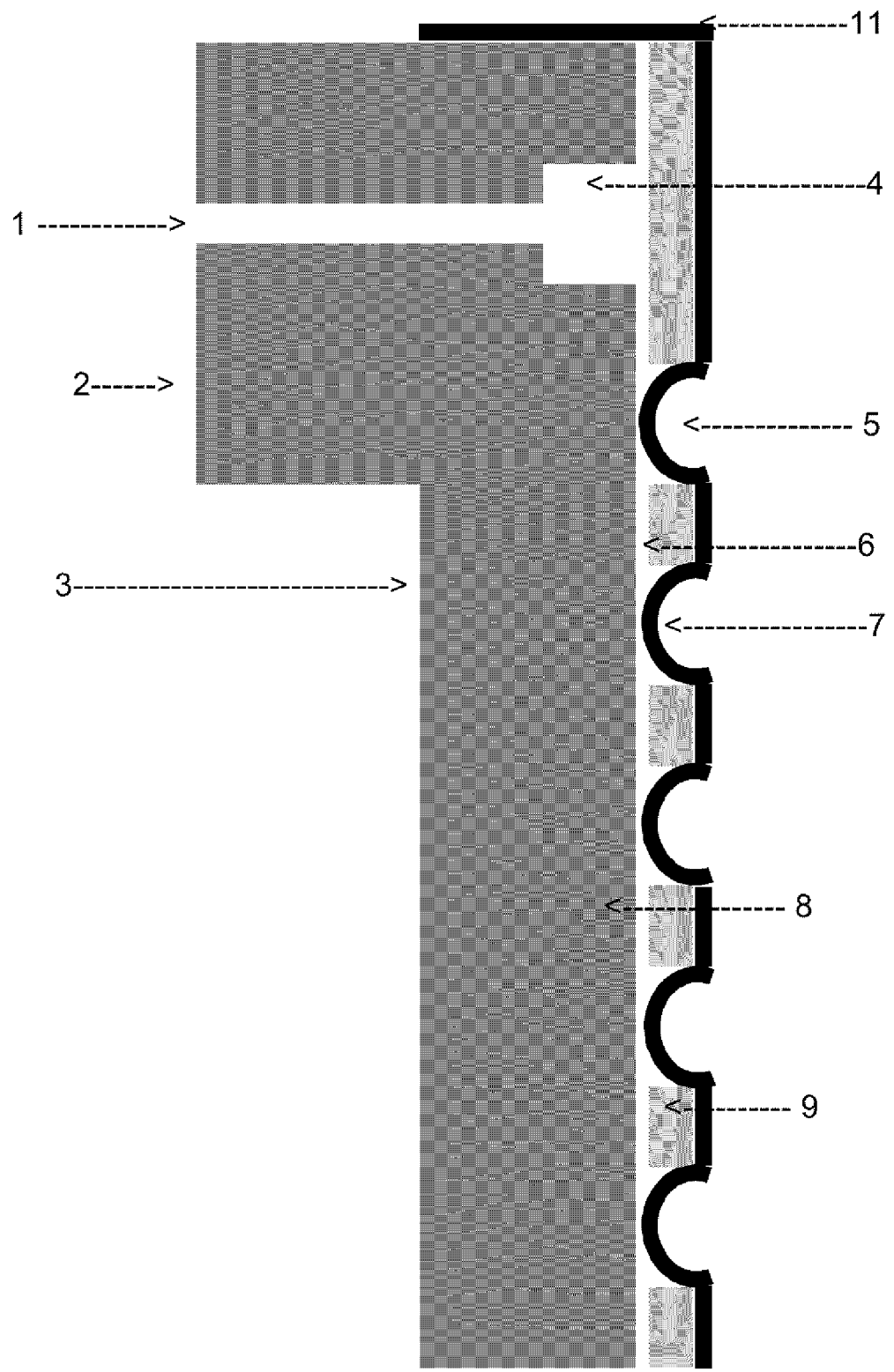
FIG. 2 is a vertical cross section of the coated reactor after having been put into service.
Figure 3:
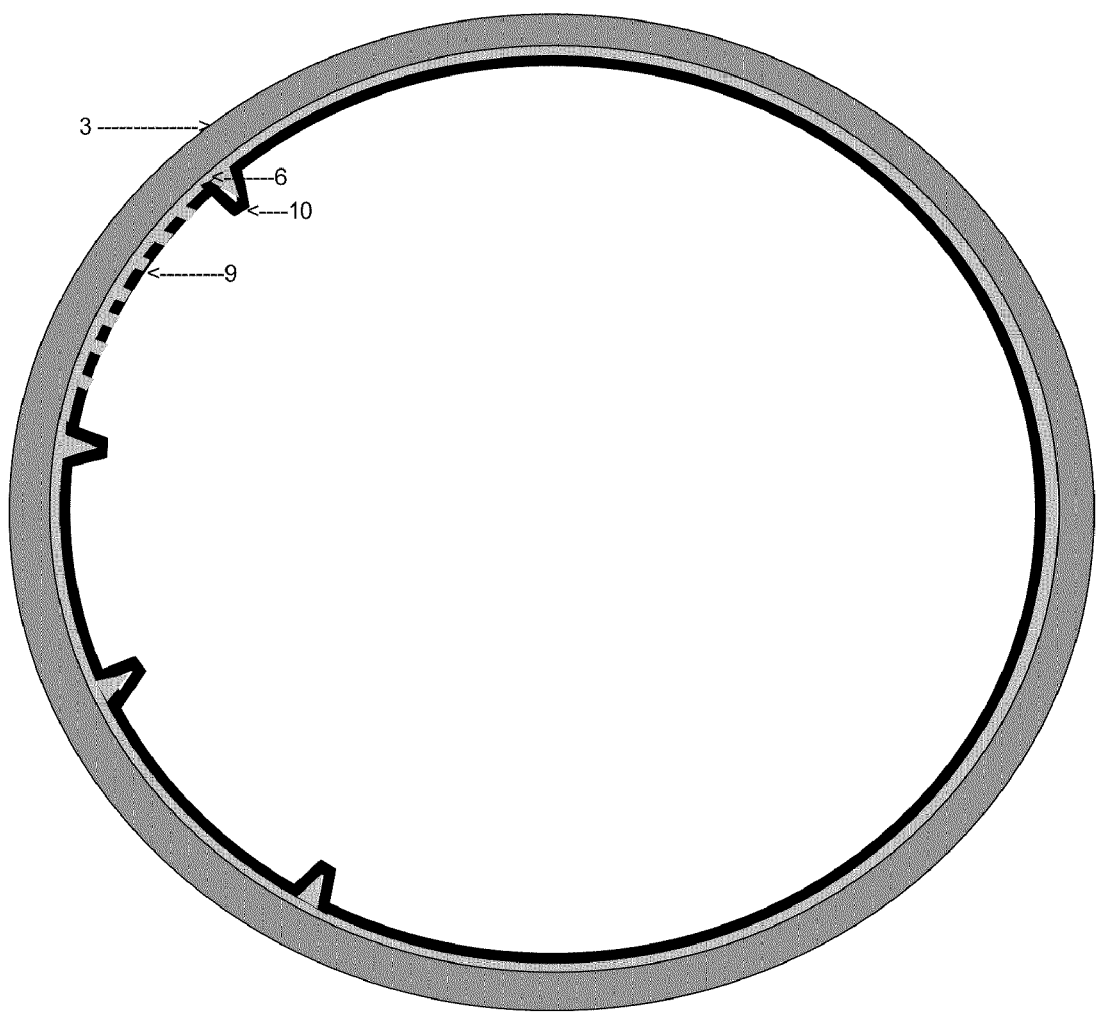
FIG. 3 is a horizontal cross section of the reactor chamber with the perforated sheet provided with ribs.

One particular embodiment of the invention is illustrated with the aid of FIGS. 1 to 3.

The face of the perforated sheet (9) comprising ribs (10) is adjusted and fastened, via several welding spots, to the inner metal wall (8) of the chamber (3) of a reactor, provided with orifices connected together by conduits.

A coating (7) composed of FEP plates, welded together is placed against the free face of the perforated sheet thus fastened.

A groove (4) is machined level with the clamp of the chamber seal (2) and makes it possible to collect the gases originating from the free space (6) between the inner wall (8) and the perforated sheet (9) comprising holes (5) and to connect this free space to the pressure control device via the orifice (1).

The upper edge of the coating is formed as a 90° flared flange (11).

The pressure that exists in the free space created between the inner metal wall of the reactor is then controlled using a vacuum pump or by introducing an inert gas, via the orifice (1), so as to ensure that this pressure is maintained at a value below that that exists inside the reactor.

The reactor is put into service by pressurizing it (1 to 10 bar absolute), then bought, by virtue of a heating jacket, to a temperature between 130 and 160° C. This heating makes it possible to soften the coating and thus to ensure an incrustation of the coating in the holes of the perforated sheet. Finally, the reactor is cooled but maintained under the same pressure.

Examples

Test Materials for Testing the Coating
  An FEP plate having a thickness of 2.3 mm and a size of 21 cm by 30 cm.
  A 316L stainless steel plate having a thickness of 5 mm and a size of 25 cm by 36 cm comprising a jacket with circulation of hot oil over its inner face (simulation of the inner wall of the reactor) and a central orifice connected to a vacuum pump.
  A metal frame of internal dimensions 19 cm by 28 cm (external dimensions 25×36 cm) which can be screwed at several points to the upper face of the stainless steel plate.
  A perforated sheet metal plate made of steel sold by Gantois under the reference R 25 T 33 and having the following features:
    Dimensions: 21 cm by 30 cm;
    Thickness: 3 mm;
    Diameter of the holes: 2.5 cm; and
    Number of holes (on the inside of the frame): 48.
  The perimeter of the FEP plate placed on the stainless steel plate is fastened to said stainless steel plate in a rigid and impervious manner by screwing the metal frame over the FEP plate.
  The inner face of the stainless steel plate is provided with a jacket with circulation of hot oil that thus makes it possible to heat it. An orifice at the centre of the stainless steel plate connects to a pipe that makes it possible to draw a vacuum between the FEP plate and the stainless steel plate.

Comparative Test:
  The FEP plate positioned as above was heated under vacuum and up to 160° C. and a deformation was observed under the effect of the expansion. Since the edges of the FEP plate were clamped, folds appeared level with the frame. Furthermore, these folds remained after cooling under pressure.

Test Conforming to the Invention:

The perforated sheet metal plate made of steel was sandwiched between the FEP plate and the solid stainless steel plate and the assembly was clamped in the metal frame.

The test was carried out as before (that is to say: under vacuum and by heating the stainless steel plate to 160° C.).

It was observed that under the action of the vacuum (in the space created between FEP and stainless steel plate) and of the softening of the FEP at high temperature, the FEP plate sank into the holes of the sheet until it touched the stainless steel sheet. Furthermore, no other deformation was observed and no folds appeared at the edge of the frame.

After cooling under vacuum, the FEP plate remained completely flat and slightly incrusted in each hole.

At the end of three successive cycles of heating at 160° C. then cooling under vacuum, there was still no damage observed.

The deformation of the FEP under the action of the expansion had therefore clearly been contained in the vicinity of the holes and had not propagated over the entire surface of the plate leading, as in the preceding test, to the formation of folds.

The anchoring of the FEP plate is thus very effective and makes it possible to ensure correct operation of the coating at high temperature.

Material for the Laboratory Implementation of the Fluorination Reaction

A one-liter reactor comprising a 316L stainless steel chamber, having an internal diameter of 100 mm and a height of 153 mm, in which a circular groove having a width of 5 mm and a depth of 2 mm was machined at the top of the chamber (level with the clamp for fastening the lid). A hole with a diameter of 2 mm was made in the clamp, which connected the groove to the outside of the chamber.

A cylinder made of perforated stainless steel sheet (thickness: 2 mm, diameter of the holes: 3 mm, four holes per cm$^2$) having an external diameter of 100 mm and a height of 110 mm. This cylinder is fitted to the inside of the chamber.

An FEP coating, composed of a cylinder obtained by welding an FEP plate having a thickness of 1.5 mm, a 1.5 mm FEP curved base welded to the lower end of the cylinder and a 45° flared flange obtained by thermoforming the upper end of the cylinder. This coating was adjusted to the inside of the cylinder made of the perforated sheet.

The pressure behind the coating was maintained during all the tests at atmospheric pressure, no leakage was observed at the outlet of the orifice made in the wall of the reactor.

Batch Fluorination Reaction of Dichloromethane:

The reactor formed in this way was loaded with 120 g of SbCl$_5$, 160 g of anhydrous HF and 170 g of CH$_2$Cl$_2$, and heated at 90° for 5 h. HCl was released and the pressure was set at 9 bar.

The DC (degree of conversion of the dichloromethane) was 83%, the F31 (chlorofluoromethane) selectivity was 9.4% and the F32 (difluoromethane) selectivity was 90.5%.

Batch Fluorination Reaction of Perchloroethylene (PER):

The reactor formed in this way was loaded with 150 g of SbCl$_5$, 300 g of HF and 83 g of PER. It was heated at 100° C. for 6 h under a pressure of 13 bar with release of HCl.

The DC (degree of conversion of PER) was 99.9% and the F123 (dichlorotrifluoroethane) selectivity was 96.3%.

These tests were carried out 18 times for CH$_2$Cl$_2$ and eight times for PER. After dismantling the reactor and the perforated sheet no corrosion of the inner wall of the reactor was observed.

These tests show that the FEP coating is impervious to the very corrosive reaction medium under fluorination reaction conditions in the liquid phase under pressure and at high temperature.

The reactor formed in this way makes it possible to efficiently carry out fluorination reactions.

What is claimed is:

1. A coated reactor comprising an inner metal wall and a fluoropolymer coating having a thickness of from about 1 to 10 mm anchored to said inner metal wall by direct physical attachment to both (a) a perforated metal sheet having a thickness of from about 1 to 10 mm and perforation openings covering from about 10 to 50% of the total surface area of said perforated metal sheet located between the inner metal wall and the fluoropolymer coating; and (b) said inner metal wall by extending through said perforations wherein a face of said perforated metal sheet is in contact with the inner metal wall of the reactor and having sufficient roughness to form a free space for gases between it said perforated metal sheet and the inner metal wall of the reactor; and means to maintain the pressure in the free space below the pressure in the reactor.

2. The reactor as claimed in claim 1, characterized in that the fluoropolymer is a copolymer of tetrafluoroethylene and of hexafluoropropylene.

3. The reactor as claimed in claim 1, characterized in that the inner metal wall of the reactor has orifices therein.

4. The reactor as claimed in claim 1, characterized in that the perforated metal sheet is provided with vertical ribs.

5. The reactor as claimed in claim 1, characterized in that one or more circular grooves are formed in the inner wall of the reactor.

6. The reactor as claimed in claim 1, characterized in that the fluoropolymer coating further comprises carbon nanotubes.

7. The reactor as claimed in claim 1, characterized in that the thickness of the fluoropolymer coating is from 1.5 to 5 mm.

8. The reactor as claimed in claim 1, characterized in that the thickness of the perforated sheet is from 3 to 6 mm.

9. The reactor as claimed in claim 1, characterized in that the perforations represent between 30 and 40% of the total surface area of the perforated metal sheet.

* * * * *